US00PP31746P2

(12) United States Plant Patent
Cain

(10) Patent No.: US PP31,746 P2
(45) Date of Patent: May 12, 2020

(54) GRAPEVINE PLANT NAMED 'IFG FORTY-TWO'

(50) Latin Name: ***Vitis interspecific* hybrid**
Varietal Denomination: IFG Forty-two

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 16/501,402

(22) Filed: Apr. 9, 2019

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 5/0812
See application file for complete search history.

(56) References Cited

U.S. PATENT DOCUMENTS

PP20,377 P2 10/2009 Cain

*Primary Examiner* — Kent L Bell

(57) ABSTRACT

This invention is a new and distinct grapevine variety denominated 'IFG Forty-two'. The new grapevine is characterized by producing naturally large size narrow ellipsoid seedless green berries having an extremely crisp texture, thin skin and which ripen in mid-season. Berries are borne on medium size clusters which are naturally loose and do not require gibberellin to thin.

1 Drawing Sheet

Latin name of the genus and species claimed: *Vitis interspecific* hybrid.

Variety denomination: 'IFG Forty-two'.

BACKGROUND OF THE INVENTION

The new and distinct Grapevine plant described and claimed herein originated from a hand pollinated cross of the interspecific hybrid 'Arkansas 2756' and 'IFG 104-253' (U.S. Plant Pat. No. 20,377) hybridized in May 2008. The abortive seed traces were subsequently embryo cultured and the resulting 107 seedlings were planted in the field in April 2009. The present variety of grapevine was selected as a single plant in September 2011 and was first asexually propagated by hardwood cuttings in December 2011 near Delano, Kern County, Calif. These resulting cuttings produced second generation plants that were planted during April 2012 near Delano, Kern County, Calif. and were observed for five years and found to reproduce true-to-type.

BRIEF SUMMARY OF THE INVENTION

The new grapevine 'IFG Forty-two' is characterized by producing naturally large size narrow ellipsoid seedless green berries having an extremely crisp texture, thin skin and which ripen in mid-season. Berries are borne on medium size clusters which are naturally loose and do not require gibberellin to thin. Berries are responsive to Gibberellic acid applications to increase berry size. To the inventor's knowledge, the known variety to which the new grapevine variety is most similar is the 'IFG Ten' (U.S. Plant Pat. No. 24,583). 'IFG Forty-two' differs from the 'IFG Ten' by having a narrow ellipsoid shape as opposed to the obtuse ovate shape of 'IFG Ten', by having more crisp flesh texture, by having somewhat weaker berry attachment and by being slightly more prone to flesh browning. 'IFG Forty-two' differs from its maternal parent, the 'Arkansas 2756' by producing larger more narrow ellipsoid berries as opposed to the smaller more oval berries of 'Arkansas 2756', by having a more yellow-green color as opposed to the darker green color of 'Arkansas 2756', and by exhibiting less flesh browning than 'Arkansas 2756'. It differs from its pollen parent, the 'IFG 104-253', by producing smaller more narrow ellipsoid berries as opposed to the larger, longer more elongated elliptic berries of 'IFG 104-253'. 'IFG Forty-two' has crisper more dense flesh than 'IFG 104-253'.

BRIEF DESCRIPTION OF THE DRAWING

The accompanying photographic drawing illustrates in full color 'IFG Forty-two'. The photograph was taken outdoors with indirect lighting. The colors are as nearly true as is reasonably possible in a color representation of this type.

The left side of the drawing has a mature leaf.

A mature fruit cluster is represented in the center of the drawing along with a typical berry in cross section.

A young shoot tip can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2016 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 'IFG Forty-two' plants grown in the vicinity of Delano, Kern County, Calif. during 2017 and 2018 and is believed to apply to plants of the variety grown under similar conditions of soil and climate elsewhere:

VINE

General:
- *Vigor*.—Vigorous.
- *Density of foliage*.—Dense.
- *Productivity*.—Very productive, producing about 29.3 to 44.0 kg of fruit per vine.
- *Root stock*.—Own root.
- *Training method*.—Typically spur pruned leaving 2 bud spurs.

Trunk:
- *Trunk diameter of 5-year-old vines at 30 cm above the soil line*.—About 8.0 cm.
- *Shape*.—Stocky.
- *Straps*.—Very long, continuous.
- *Surface texture*.—Shaggy texture.
- *Inner bark color*.—Greyed-orange: 165A.
- *Outer bark color*.—The following colors were observed: Brown: N200C and N200D.

SHOOTS

Young shoot:
- *Form of tip*.—Wide open.
- *Distribution of anthocyanin coloration of tip*.—Absent.
- *Intensity of anthocyanin coloration of tip*.—Absent.
- *Density of prostrate hairs of tip*.—Sparse to medium.
- *Density of erect hairs on tip*.—Absent or very sparse.
- *Color*.—Yellow-green: 144A.

Woody shoot (mature canes):
- *Internode length*.—Medium: About 13.6 cm.
- *Width at node*.—About 2.0 cm.
- *Cross section*.—Circular to slightly elliptic.
- *Surface*.—Smooth.
- *Main color*.—The following colors were observed: Greyed-orange: 165A and 165B.
- *Density of erect hairs on nodes*.—Sparse.
- *Density of erect hairs on internodes*.—Sparse to medium.
- *Axillary shoot vigor at full bloom*.—Weak to medium.

Flowering shoot:
- *Vigor during flowering*.—Strong.
- *Attitude during flowering on shoots not tied*.—Erect.
- *Color*.—Dorsal side of internodes — Yellow-green: 144A.
- *Color*.—Ventral side of internodes — Yellow-green: 144A.
- *Color*.—Dorsal side of nodes — Yellow-green: 144A.
- *Color*.—Ventral side of nodes — Yellow-green: 144A.
- *Density of prostrate hairs on nodes*.—Sparse.
- *Density of erect hairs on nodes*.—None to very sparse.
- *Density of prostrate hairs on internode*.—Sparse.
- *Density of erect hairs on internode*.—None.
- *Anthocyanin coloration of buds*.—Absent.

Tendrils:
- *Distribution on the shoot (at full flowering)*.—Discontinuous.
- *Color*.—Yellow-green: N144D.
- *Form*.—Mostly bifurcated with a few trifurcated.
- *Number of consecutive tendrils*.—2.

LEAVES

Young leaves:
- *Color of upper surface of first four distal unfolded leaves*.—Yellow-green: 144A.
- *Color of lower surface of young leaves*.—Yellow-green: N144A.
- *Average intensity of anthocyanin coloration of six distal leaves prior to flowering*.—Absent.
- *Density of prostrate hairs between veins (lower surface)*.—Very sparse.
- *Density of prostrate hairs on veins (lower surface)*.—Sparse.
- *Density of erect hairs between veins (lower surface)*.—Absent.
- *Density of erect hairs on veins (lower surface)*.—Very sparse.

Mature leaves (opposite first cluster):
- *Average length*.—About 14.1 cm.
- *Average width*.—About 17.7 cm.
- *Mature leaf size*.—Medium.
- *Shape of blade*.—Wedge-shaped.
- *Number of lobes*.—5.
- *Blade venation*.—Palmate.
- *Average intensity and color of anthocyanin coloration of main veins on upper side of blade*.—Absent.
- *Mature leaf profile*.—Flat.
- *Blistering surface of blade upper surface*.—Very weak.
- *Leaf blade tip*.—In the plane of the leaf.
- *Leaf apex*.—Acute.
- *Leaf margin*.—Serrate.
- *Undulation of margin*.—Slight.
- *Undulation of blade between main and lateral veins*.—Only near margin.
- *Shape of teeth*.—Mixture of both sides straight and both sides convex.
- *Length of teeth*.—Medium.
- *Ratio length/width of teeth*.—Medium.
- *Shape of upper lateral sinuses*.—Open.
- *Depth of upper lateral sinuses*.—Shallow.
- *General shape petiole sinus*.—Half open.
- *Shape of base of upper leaf sinuses*.—V-shaped.
- *Tooth at petiole sinus*.—Absent.
- *Density of prostrate hairs between veins on lower surface of blade*.—Sparse.
- *Density of erect hairs between veins on lower surface of blade*.—Dense.
- *Density of prostrate hairs on main veins on lower surface of blade*.—Sparse.
- *Density of erect hairs on main veins on lower surface of blade*.—Very dense.
- *Density of prostrate hairs on main veins on upper surface of blade*.—Sparse.
- *Density of erect hairs on main veins on upper surface of blade*.—None or very sparse.
- *Autumn coloration of leaves*.—The following colors were observed: Greyed-yellow: 162B and 162C.

Upper surface:
- *Color*.—Green: 137A.
- *Anthocyanin coloration of main veins (lower surface)*.—Absent.
- *Color of main veins*.—Yellow-green: 145A.

*Surface appearance*.—Semi-glossy.
*Blistering surface of blade*.—Weak.
Lower surface:
*Color*.—Yellow-green: 146B.
*Anthocyanin coloration of main veins* (*lower surface*) .—Absent.
*Color of main veins*.—Yellow-green: 147D.
*Glossiness*.—Weak.
*Surface texture*.—Smooth.
*Surface appearance*.—Dull.
Petiole:
*Length*.—About 13.5 cm.
*Diameter of petiole* 2 *cm from blade*.—About 3.7 mm.
*Petiole color*.—Yellow-green: 145B.
*Length of petiole compared to middle vein*.—Slightly shorter.
*Density of prostrate hairs on petiole*.—None to sparse.
*Density of erect hairs on petiole*.—Medium to dense.
Buds:
*Bud fruitfulness*.—Basal: mostly fruitful.
*Position of first fruitful shoot on previous season cane*.—$1^{st}$ to $2^{nd}$ node.
*Dormant bud length*.—About 11.0 mm.
*Dormant bud width in the proximal/distal plane*.—About 9.5 mm.
*Dormant bud color*.—Greyed-orange: 165A.
*Time of bud burst*.—Mid-season: About Mar. 21, 2018.

FLOWERS

General:
*Flower sex*.—Hermaphrodite.
*Length of single flower, unopened*.—About 3.5 mm.
*Width of single flower*.—Unopened: About 1.9 mm. Opened: About 7.7 mm.
*Stamen length*.—About 3.6 mm.
*Stamen count*.—5.
*Pollen color*.—Yellow: 10B.
*Pistil length*.—About 2.3 mm.
*Pistil color*.—Yellow-green: 144A.
*Position of first flowering and fruiting node*.—$3^{rd}$ to $4^{th}$ node (current season growth).
*Number of inflorescence per flowering shoot*.—1.1 to 2: About 1.7.
*Time of bloom*.—Mid-season as compared with similar varieties in the growing area of Delano, Calif.
*Date of full bloom*.—About May 9, 2018.

FRUIT

General:
*Ripening period*.—Late: approximately Oct. 12, 2017.
*Use*.—Fresh market.
*Keeping quality*.—Excellent, remains commercially acceptable when stored up to 8 weeks at 0° C. and high relative humidity.
*Resistance to*.—Insects: Average typical of *Vitis vinifera* species. Diseases: Average typical of *Vitis vinifera* species.
*Refractometer test*.—Soluble solids: About 22.0 Brix.
*Brix/acid*.—About 62.9.
*Titratable acidity*.—About 0.35.
*Juice ph*.—About 4.06.
*Juice color*.—Yellow-green: 150C.
Cluster:
*Mature cluster length* (peduncle excluded).—About 25.3 cm.
*Mature cluster width*.—About 18.0 cm.
*Mature cluster weight*.—About 977 g.
*Bunch density*.—Loose: single berries, some pedicels visible.
*Number of berries*.—About 149.
*Form*.—Conical.
Peduncle:
*Lignification of peduncle*.—Weak.
*Diameter of peduncle*.—About 4.3 mm.
*Length of peduncle*.—Medium: Approximately 5.1 cm.
*Color of peduncle*.—Yellow-green: 145A.
Berry:
*Uniformity of size*.—Uniform.
*Single berry weight*.—About 7.5 g.
*Shape*.—Narrow ellipsoid.
*Seeds*.—Contains small rudimentary seed traces.
*Cross section*.—Circular.
*Berry dimensions*.—Longitudinal axis: About 3.2 cm; horizontal axis: About 2.0 cm.
*Pedicel length*.—About 6.9 mm.
*Pedicel width*.—About 1.4 mm.
*Pedicel color*.—Yellow-green: 145C.
*Berry firmness*.—Firm.
*Particular flavor*.—Neutral.
*Bloom* (*cuticular wax*).—Medium.
*Berry separation from pedicel*.—Moderately easy.
*Skin color* (*without bloom*).—The following colors were observed: Yellow-green: 144C and 145B.
*Flesh color*.—Green-white: 157C.
Skin:
*Thickness*.—Medium.
*Skin toughness*.—Not notable when chewing.
*Reticulation*.—Absent.
*Tenacity*.—Tenacious to flesh.

What is claimed:

1. A new and distinct variety of grapevine as herein illustrated and described.

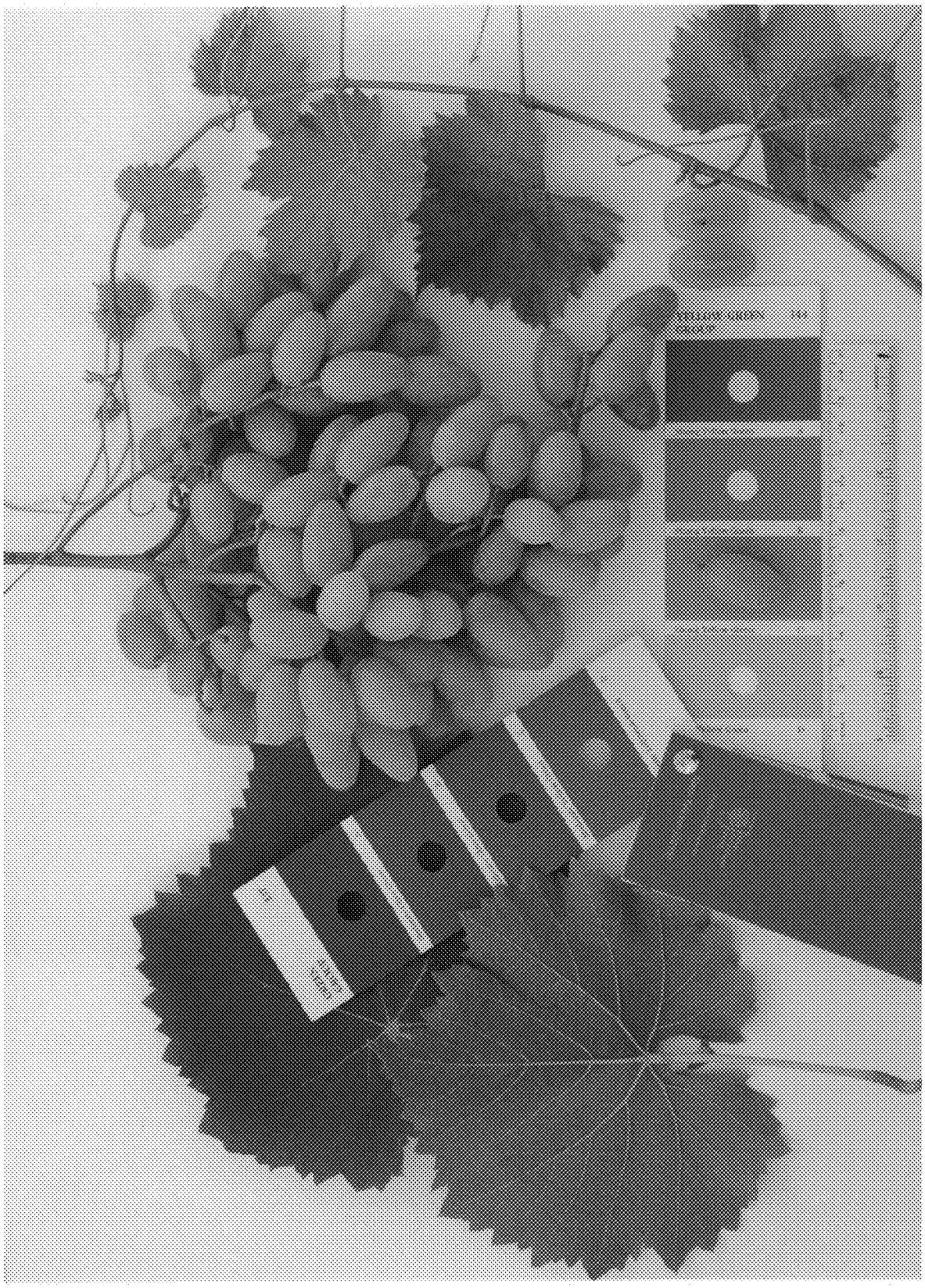

* * * * *